United States Patent
Dente et al.

(10) Patent No.: US 8,302,819 B2
(45) Date of Patent: Nov. 6, 2012

(54) COMBINATION AIR FRESHENER AND FLUID DISPENSER

(75) Inventors: Stephen V. Dente, Oakland, NJ (US); Christopher Habeck, Oakland, NJ (US)

(73) Assignee: Robertet, Inc., Oakland, NJ (US)

( * ) Notice: Subject to any disclaimer, the term of this patent is extended or adjusted under 35 U.S.C. 154(b) by 978 days.

(21) Appl. No.: 11/854,407

(22) Filed: Sep. 12, 2007

(65) Prior Publication Data

US 2008/0237248 A1 Oct. 2, 2008

Related U.S. Application Data

(60) Provisional application No. 60/844,059, filed on Sep. 12, 2006.

(51) Int. Cl.
*B67D 7/84* (2010.01)

(52) U.S. Cl. ............... 222/173; 222/153.01; 222/180; 222/192; 222/321.7; 222/321.9; 239/60; 239/289

(58) Field of Classification Search ............... 222/173, 222/179.5, 180, 192, 321.7, 321.9, 383.1, 222/385, 153.01; 239/53, 54, 60, 289

See application file for complete search history.

(56) References Cited

U.S. PATENT DOCUMENTS

| | | | |
|---|---|---|---|
| 3,488,002 A * | 1/1970 | Mina | 222/179.5 |
| 5,148,948 A | 9/1992 | Granville et al. | |
| 5,165,603 A * | 11/1992 | Hahn | 239/53 |
| 5,476,197 A * | 12/1995 | Lawrence et al. | 222/180 |
| 6,569,387 B1 * | 5/2003 | Furner et al. | 239/289 |
| 6,769,631 B2 | 8/2004 | Brown | |
| 2005/0274819 A1 * | 12/2005 | Reed et al. | 239/60 |

* cited by examiner

*Primary Examiner* — Frederick C. Nicolas

(74) *Attorney, Agent, or Firm* — Fish & Richardson P.C.

(57) ABSTRACT

An assembly includes a fluid dispenser, an engagement feature on a portion of the fluid dispenser and a fragrance element with one or more surfaces that define an opening through the fragrance element, wherein the portion of the fluid dispenser with the engagement feature can extend through the opening in the fragrance element to engage a mounting base on an opposite side of the fragrance element.

27 Claims, 4 Drawing Sheets

COMBINATION AIR FRESHENER AND FLUID DISPENSER

CROSS-REFERENCE TO RELATED APPLICATION(S)

This application claims the benefits of and priority to U.S. Provisional Patent Application Ser. No. 60/844,059, filed on Sep. 12, 2006, the disclosure of which is incorporated herein by reference in its entirety.

TECHNICAL FIELD

This invention relates to an air freshener and, more particularly, to a combination air freshener/fluid dispenser.

BACKGROUND

Fluid dispensers, such as liquid soap dispensers, and air fresheners are frequently found in the same location. As an example, an airplane restroom typically includes a liquid soap dispenser as well as an air freshener.

SUMMARY OF THE INVENTION

In one aspect, an assembly includes a fluid dispenser, an engagement feature (e.g., threads) on a portion of the fluid dispenser and a fragrance element with one or more surfaces that define an opening through the fragrance element. The portion of the fluid dispenser with the engagement feature is adapted to extend through the opening in the fragrance element to engage a mounting base on an opposite side of the fragrance element.

In some implementations, the fragrance element is an absorbent material permeated with a fragrance. The absorbent material may be a porous polyethylene, paper, compressed wood or any other absorbent material that can be suitably shaped to be coupled to the assembly. In some implementations, the fragrance element includes sodium bicarbonate (i.e., baking soda) and/or may be permeated with a malodor counteracting ingredient.

In a typical implementation, the fragrance element is adapted to provide, when assembled in the assembly, a generally acceptable scent level in a room for about as long as the fluid dispenser is expected to contain dispensable fluid. The absorbent material may be permeated with fragrance to between approximately 10% and 30% of its capacity. More preferably, the absorbent material is permeated with fragrance to about 20% of its capacity.

Certain embodiments of the fragrance element have an outer diameter that is smaller than a corresponding outer diameter of a portion of the container just above the fragrance element and/or a smaller diameter than a corresponding outer diameter of a portion of the mounting base just below the fragrance element. Accordingly, when a person grips the assembly near the fragrance element, the person is substantially prevented from contacting the fragrance element. More particularly, the outer diameter of the fragrance element may be between about 70% and 95% of the corresponding outer diameter of the fluid dispenser and/or the corresponding diameter of the mounting base. More preferably, the outer diameter of the fragrance element is about 90% of those corresponding diameters.

In another aspect, an assembly includes a mounting base for a fluid dispenser, a fluid dispenser with a threaded protrusion adapted to engage the mounting base, and a substantially annular fragrance element with surfaces that define an opening through which the threaded protrusion can extend. The fragrance element is positioned around the threaded protrusion and in contact with the mounting base.

In yet another aspect, an assembly includes a fluid dispenser having a container, a threaded protrusion formed on the container and a mounting base for the fluid dispenser. The mounting base has a threaded opening adapted to engage the threaded protrusion formed on the container. The assembly also includes a fragrance element with one or more surfaces that define an opening. The threaded protrusion extends through the opening in the fragrance element and engages the threaded opening in the mounting base.

In some implementations, one or more of the following advantages may be present.

By combining fluid dispensing and air freshening into a single device, space may be efficiently utilized. This may be particularly significant in areas where there is a limited amount of space available, such as in restrooms onboard airplanes, boats or trains. Additionally, a fragrance element in an air freshener can be designed to remain fragrant for about as long as the fluid in the dispenser is expected to last. For example, if a supply of soap in a liquid soap dispenser is expected to last for about 3-4 days, a fragrance element associated with that soap dispenser could be designed to last about 3-4 days as well. In that situation, when the fluid dispenser is ready to be replaced, the fragrance element also will be ready to be replaced. Both items can be replaced at the same time, as a single unit. This may reduce the burden on maintenance personnel, for example, in restrooms onboard airplanes, trains, ships, etc.

Also, in some implementations, the fragrance element is advantageously connected to the fluid dispenser in a manner that enables the release fragrance into the air, but minimizes the possibility that a person might accidentally touch the fragrance element. This could avoid causing skin irritation, for example, to a restroom patron.

The details of one or more embodiments are set forth in the accompanying drawings and the description below. Other features and advantages will be apparent from the description and drawings, and from the claims.

BRIEF DESCRIPTION OF THE DRAWINGS

Like reference numerals refer to like elements.

DETAILED DESCRIPTION

Figure 1:
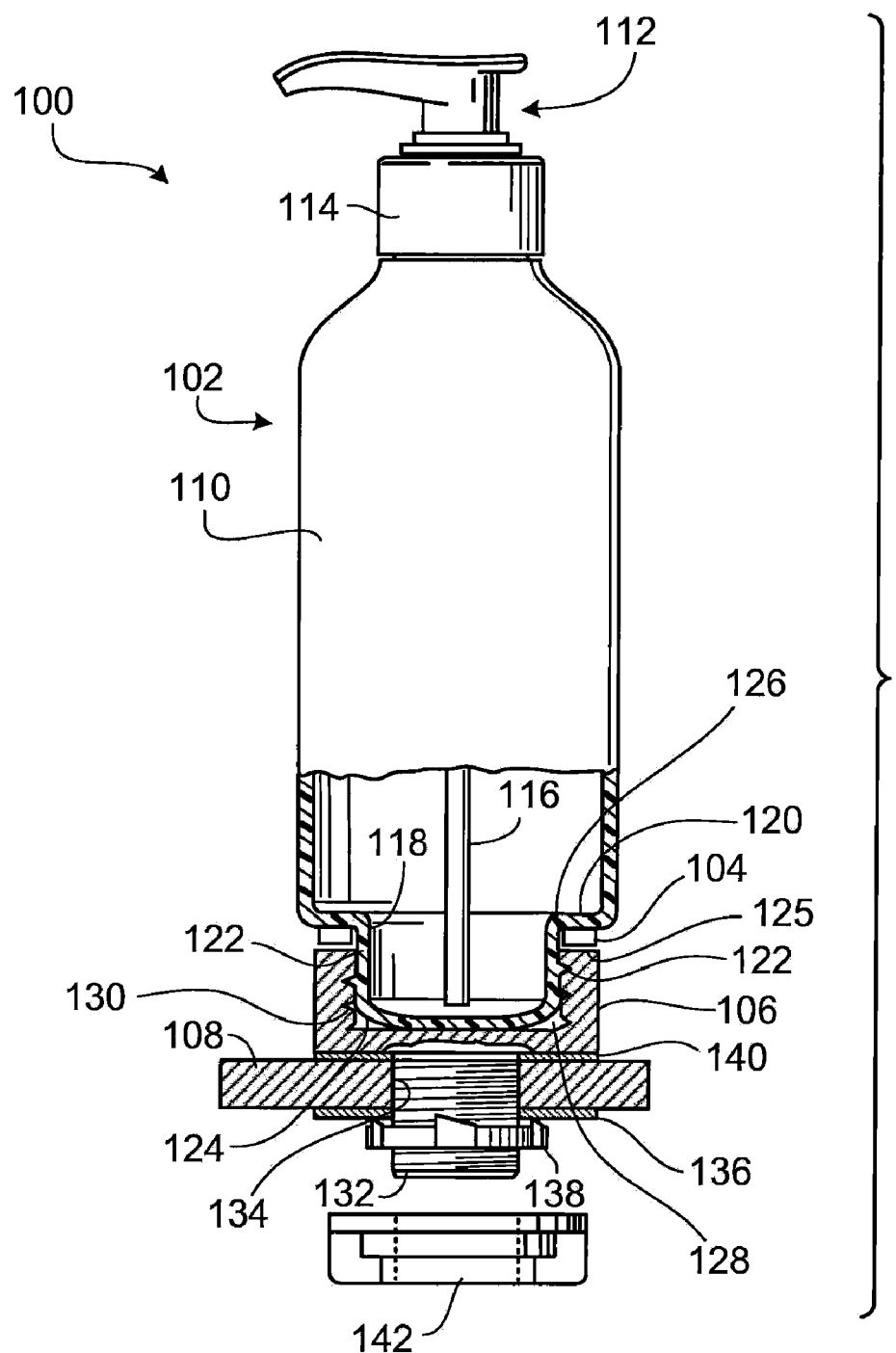
FIG. 1 is a side elevation view, partly in section, illustrating one embodiment of a fluid dispenser/air freshener assembly.

FIG. 1 is a side elevation view, partly in section, illustrating one embodiment of a fluid dispenser/air freshener assembly 100.

The illustrated assembly 100 includes a counter 108, a mounting base 106 attached to the counter 108 such as are typically found in an airplane restroom, a fluid dispenser 102 that includes a threaded portion screwed into the mounting base 106 and an annular fragrance element 104 disposed around the threaded portion of the fluid dispenser 102 and above the mounting base 106. The illustrated fragrance element 104 is adapted to freshen and deodorize the air around it.

In a typical implementation, the fragrance element 104 is an absorbent material that is permeated with a fragrance. The absorbent material can be porous polyethylene, paper, compressed wood or any other absorbent material that can be suitably shaped. In some implementations, sodium bicarbonate (i.e., baking soda) is added to either the absorbent material or to the fragrance to further enhance odor reduction.

Typically, the fragrance element 104 is specifically designed and the fragrance is specifically formulated according to the expected service requirements of the combination air freshener/fluid dispenser. More particularly, fragrance may be applied to the absorbent material in such a manner that the fragrance element will provide a generally acceptable scent level in a given room for about as long as the fluid supply in the fluid dispenser is expected to last under ordinary service conditions. Accordingly, when the fluid supply has been depleted and the fluid dispenser requires replacement, the fragrance element also will be ready for replacement. When that happens, a person may easily replace both elements at the same time.

The absorbent material of the fragrance element 104 may be permeated with a fragrance oil to between approximately 10% and 30% of the absorbent material's capacity. More preferably, the absorbent material may be permeated with a fragrance oil to about 20% of its capacity. Some examples of fragrance oils include citrus R07-5000, Floral R07-5001, Lavender R07-5002 and Fruity R07-5003. In some implementations, the fragrance oil includes one or more malodor counteraction ingredient. Examples of malodor counteraction ingredients are disclosed in U.S. Pat. Nos. 4,840,792 and 5,795,566, the disclosures of which are hereby incorporated by reference.

The illustrated fluid dispenser 102 is securely mounted to the counter 108 and, as such, is well suited for use in bathrooms onboard moving vehicles, such as airplanes and trains. The fluid dispenser 102 includes a container 110, a manually actuated pump and spout assembly 112 coupled to a cap 114 that is threaded onto the neck of the container 110. The pump and spout assembly 112 includes a dip tube 116 that extends to near the bottom of the container 110, whereby measured amounts of liquid, such as soap, hand lotion, and the like, can be dispensed by manually pushing downwardly and releasing the pump and spout assembly 112. An integral, substantially cylindrical protrusion 118 is formed at a bottom of the container 110 and extends downward. The protrusion 118 has a smaller outer diameter than the portion of the container 110 directly above the protrusion 118. An annular, horizontally disposed lip 120 is formed where the container 110 turns inward near the top of the protrusion 118.

The protrusion 118 includes engagement features 122 formed at an outer surface thereof. The illustrated engagement features 122 are external threads that are adapted to screw into corresponding threads on an inner surface of an opening in the mounting base 106. The protrusion 118 has a substantially convex bottom surface 124, which prevents the fluid dispenser 102 from supporting itself in an upright position unless it is screwed into a support member, such as the illustrated mounting base 106.

Since the illustrated fragrance element 104 is substantially annular, it includes surfaces that define a opening 126 through the fragrance element 104. The opening 126 is approximately centrally disposed in the fragrance element 104 and is sufficiently large that the threaded protrusion 118 on the container 110 can pass through it. In some implementations, the opening 126 is sized so that a friction fit is achieved between the threaded protrusion 118 and the fragrance element 104. In those instances, the fragrance element 104 may be held in place by friction when it is coupled to the threaded protrusion 118.

In the illustrated implementation, the protrusion 118 passes through the opening 126 and engages the mounting base 106 at an opposite side of the fragrance element 104. In the illustrated implementation, the fragrance element 104 is positioned between the annular lip 120 of the container 110 and an annular surface 125 at an upper portion of the mounting base 106.

The mounting base 106 is positioned beneath the fragrance element 104 and has surfaces that define an opening 128 that faces upward. The opening 128 is adapted to receive the protrusion 118 and has engagement features 130 (e.g., threads) that are adapted to engage the corresponding engagement features 122 (e.g., threads) 122 of the protrusion 118. In the illustrated implementation, the protrusion is screwed into the opening 128 in the mounting base 106.

A fastening element 132 extends from a bottom surface of the mounting base 106. In the illustrated implementation, the fastening element 132 is a threaded shaft. The threaded shaft passes through a hole 134 in the counter 108. A metal washer 136 is placed over the threaded shaft below the counter 108. A lock washer 138 is coupled to the threaded shaft below the metal washer 136. An elastomeric washer 140 is positioned between the mounting base 106 and the counter 108. To maintain the lock washer 138 and associated mounting base 106 in a fixed, locked position on the counter 108, a wing nut 142 is threaded onto the lower end of the threaded shaft and fastened up against the lock washer 138.

Figure 2:
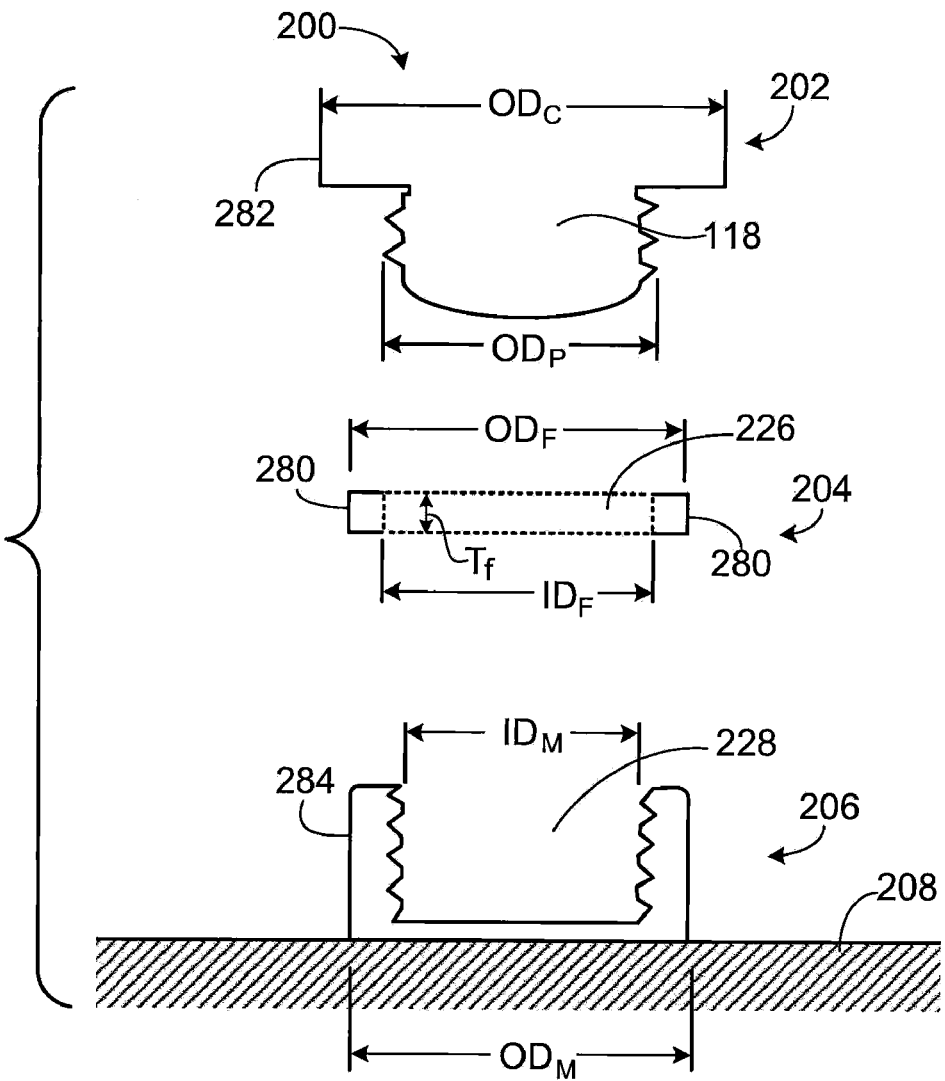
FIG. 2 is a partial side sectional exploded view of an implementation of a fluid dispenser/air freshener assembly identifying dimensions of certain components in the assembly.

FIG. 2 is a partial side sectional exploded view of an implementation of a fluid dispenser/air freshener assembly 200 identifying dimensions of certain components in the assembly. The illustrated components include a fluid dispenser 202, a fragrance element 204 and a mounting base 206.

The illustrated fragrance element 204 has an outer diameter $OD_f$ and a thickness $T_f$. There is a centrally disposed opening 226 in the fragrance element 204 that extends axially through the fragrance element 204. That centrally disposed opening 226 has an inner diameter $ID_f$. The portion of the container 202 that is directly above the fragrance assembly when assembled has an outer diameter $OD_c$. The threaded protrusion on the container 202 has an outer diameter $OD_p$. The mounting base 206 has an outer diameter $OD_m$. The opening 228 in the mounting base 206 has an inner diameter $ID_m$.

As is typical, the illustrated fragrance element 204 is sized so that its outer diameter $OD_f$ is smaller than the corresponding outer diameter $OD_c$ of the portion of the container 210 that sits, when assembled, directly above the fragrance element 204. The illustrated fragrance element 204 also is sized so that its outer diameter $OD_f$ is smaller than the outer diameter $OD_m$ of the mounting base 206 that it sits above. In general, those dimensional relationships may be desirable to ensure that, when assembled, the outer edge 280 of the fragrance element 204 cannot be accidentally touched, for example, by a bathroom patron who casually grips the assembly. More particularly, when assembled, the outer edge 280 of the fragrance element 204 does not extend beyond the outer edge 282 of the container directly above the fragrance element 204 or the outer edge of the mounting base 206 directly below the fragrance element. Preventing a person from accidentally contacting the fragrance element 204 may be desirable, particularly if the fragrance element contains chemicals that could cause skin irritation.

In a typical implementation, the outer diameter $OD_f$ of the fragrance element 204 is between about 70% and 95% of the corresponding outer diameter $OD_c$ of the portion of the container 210 immediately above the fragrance element. More preferably, however, the outer diameter $OD_f$ of the fragrance element 204 is about 90% of the corresponding outer diameter $OD_c$ of the portion of the container 210 immediately above the fragrance element 204. Similarly, in a typical implementation, the outer diameter $OD_f$ of the fragrance element 204 is between about 70% and 95% of the corresponding outer diameter $OD_m$ of the mounting base 206 below the fragrance element 204. More preferably, however, the outer diameter $OD_f$ of the fragrance element 204 is about 90% of the corresponding outer diameter $OD_m$ of the mounting base 206 below the fragrance element 204.

The outer diameter $OD_f$ of the illustrated fragrance element 204 also is sized to be larger than the inner diameter $ID_m$ of the opening 228 in the mounting base 206. That dimensional relationship is desirable to ensure that the fragrance element 204 does not fall into the opening 228 in the mounting base 206 when assembled.

Additionally, the inner diameter $ID_f$ of the fragrance element 204 is large enough that the threaded protrusion 118 can pass through it. Typically, the inner diameter $ID_f$ is sized to be just larger than the outer diameter $OD_p$ of the threaded protrusion 118. In some instances the inner diameter $ID_f$ is sized so that a friction fit is achieved between the fragrance element and the threads on the threaded protrusion 118.

The intensity of fragrance emitted by the fragrance element 204 is generally proportional to the size of the exposed area of the outer edge 280 of the fragrance element 204. The intensity of fragrance emitted by the fragrance element 204 also is generally proportional to the amount (and volatility) of the fragrance applied to the fragrance element 204. In one implementation, the outer diameter of the fragrance element 204 is approximately 5.08 cm (i.e., 2 inches), the thickness $T_f$ is approximately 0.635 cm (i.e., ¼ inch) and the fragrance element 204 is permeated with approximately 2 grams of fragrance oil. A fragrance element with those dimensions and prepared in that manner may be suitable, for example, to freshen the air in a restroom that is approximately 5.66 m$^3$ (i.e., 200 ft$^3$) for a period of time between about 3 to 7 days.

Figure 3:
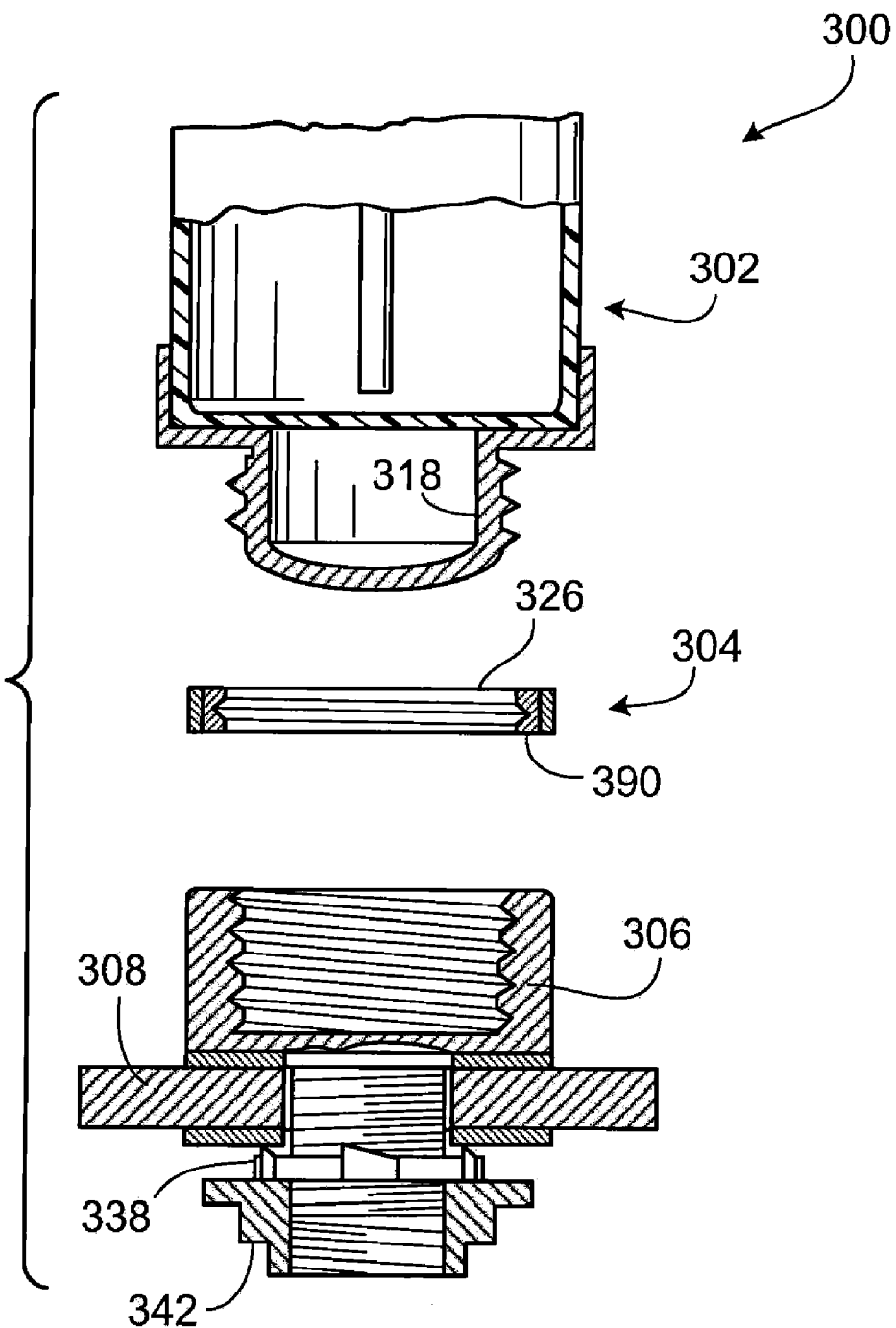
FIG. 3 is a partial side sectional exploded view of another fluid dispenser/air freshener assembly.

FIG. 3 is a partial side sectional exploded view of another fluid dispenser/air freshener assembly 300.

The illustrated assembly 300 includes a fluid dispenser 302, a fragrance element 304 and a mounting base 306 coupled to a counter 308.

The illustrated fragrance element 304 is substantially annular and has an opening 326 that extends axially through the fragrance element 304. A threaded insert 390 is positioned inside the opening 326 in the fragrance element 304 and is arranged so that it can be screwed onto the threaded protrusion 318. The threaded insert 390 may be plastic, metal or any other suitable material. The threaded insert 390 may be held in place inside the fragrance element 304, for example, by an adhesive material or substantially by friction.

Figure 4:
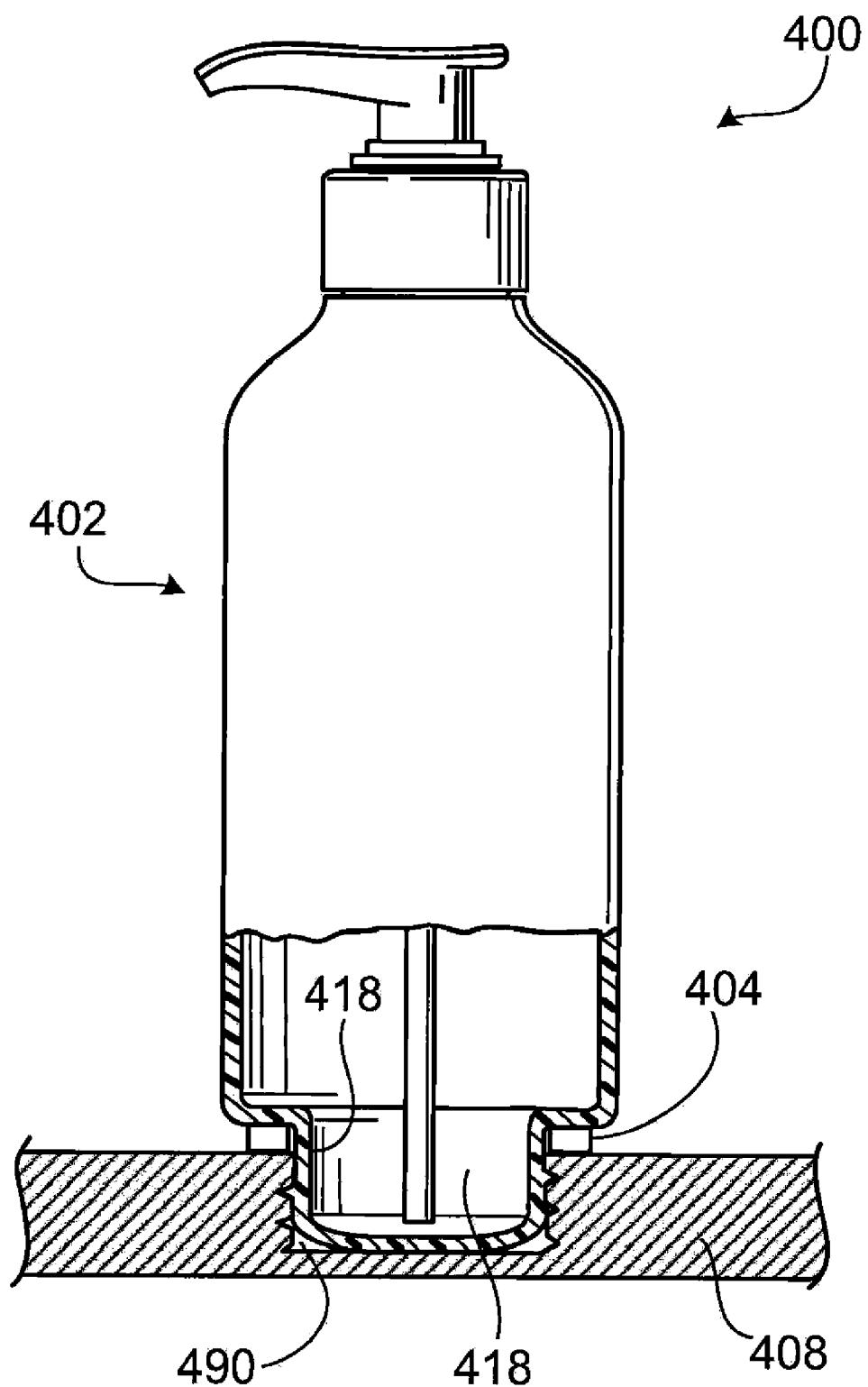
FIG. 4 is a side sectional elevation view of still another fluid dispenser/air freshener assembly.

FIG. 4 is a side sectional elevation view of still another fluid dispenser/air freshener assembly 400. The illustrated assembly 400 includes a fluid dispenser 402, a fragrance element 404 and a counter 408.

In the illustrated implementation, the threaded projection 418 on the fluid dispenser is screwed directly into a threaded hole 490 in the counter 408. Accordingly, no separate mounting base (e.g., mounting base 106) is provided. Instead, the threaded hole 490 in the counter 408 itself acts as a mounting base for the fluid dispenser 402.

An annular fragrance element 404 is positioned around the threaded projection 418 of the fluid dispenser 402 and sits just above the counter 408.

A number of embodiments of the invention have been described. Nevertheless, it will be understood that various modifications may be made without departing from the spirit and scope of the invention.

For example, although the fragrance element has been described as having an substantially annular (or washer-like) shape, the fragrance element could be a different shape, such as rectangular, triangular, or any other shape that might fit around a projection like a washer. The fragrance element could include a break so that it does not extend fully (i.e., 360°) around the projection. The fragrance element could be permeated with any of a variety of fragrance oils or substances that include fragrance or odor-eliminating characteristics. For example, in certain implementations, the fragrance element includes charcoal, zeolites and/or cyclodextrins.

Additionally, the projection on the container could be adapted to engage the mounting base (or a hole in the counter) in a number of ways other than being screwed into it. For example, the projection could be snap-fit into the mounting base/counter. Alternatively, the projection could be engaged to the mounting base/counter using an adhesive material. The projection could include any number of features formed on its outer surface to help frictionally engage the mounting base or counter. Similarly, the mounting base could be secured to the counter in a number of ways. For example, the mounting base could be adhered to the counter. Alternatively, a suction element (e.g., a suction cup) could be used to secure the mounting base to the counter. Indeed, the mounting base may be held in place relative to the counter simply by the presence of a non-stick material at an interface between the mounting base and the counter.

The liquid dispenser could be any kind of liquid dispenser. The container may be plastic, metal or any other suitable material. The liquid dispenser may be adapted to operate automatically. It may be adapted to dispense fluid in any number of ways, including pump-action, squeezing, etc. Additionally, the liquid dispenser may be adapted to be hung upside down or on a substantially vertical surface, such as a wall. In those instances, the fragrance element would be positioned between the liquid dispenser and its associated mounting elements.

The protrusion of the container that is adapted to engage the mounting base may have a diameter that is the same size as or even larger than the portion of the container above the protrusion. Moreover, although the illustrated implementations show external threads on the protrusion that engage internal threads on the mounting base, in some implementations, the mounting base has external threads that screw into internal threads in a hole on the container.

In some implementations, one or more lips (not shown) may extend either from either the container or the mounting base to at least partially cover the fragrance element. Such lip(s) may further prevent a person from accidentally touching the fragrance element. Such lip(s) would likely include openings (i.e., vents) that allow the fragrance to escape the fragrance element and enter the room.

Accordingly, other implementations are within the scope of the claims.

What is claimed is:

1. An assembly comprising:
   a fluid dispenser having an annular lip;
   an engagement feature on a portion of the fluid dispenser;

a mounting base having an annular surface that faces the annular lip when the fluid dispenser is engaged with the mounting base;

a fragrance element with one or more surfaces that define an opening through the fragrance element, wherein the portion of the fluid dispenser with the engagement feature is adapted to extend through the opening in the fragrance element and engage the mounting base, and wherein the assembly is arranged such that when the fragrance element is positioned between the annular lip of the fluid dispenser and the annular surface of the mounting base and the engagement feature on the fluid dispenser is fully engaged with the mounting base, an outer surface of the fragrance element is exposed to release fragrance outside the assembly.

2. The assembly of claim 1 wherein the mounting base comprises a fastening element adapted to secure the mounting base to a counter.

3. The assembly of claim 2 wherein the fastening element comprises:
a threaded shaft adapted to pass through an opening in the counter and
a nut coupled to the threaded shaft.

4. The assembly of claim 1 wherein the fragrance element comprises an absorbent material permeated with a fragrance.

5. The assembly of claim 4 wherein the absorbent material is a porous polyethylene.

6. The assembly of claim 4 wherein the absorbent material is paper.

7. The assembly of claim 4 wherein the absorbent material is compressed wood.

8. The assembly of claim 4 wherein the fragrance element comprises sodium bicarbonate.

9. The assembly of claim 4 wherein the absorbent material is further permeated with a malodor counteracting ingredient.

10. The assembly of claim 4 wherein the absorbent material is permeated with fragrance to between approximately 10% and 30% of its capacity.

11. The assembly of claim 10 wherein the absorbent material is permeated with fragrance to about 20% of its capacity.

12. The assembly of claim 1, wherein the fragrance element has an outer diameter that is smaller than a corresponding outer diameter of a portion of the fluid dispenser just above the fragrance element and smaller than a corresponding outer diameter of a portion of the mounting base just below the fragrance element,
such that when a person grips the assembly near the fragrance element, the portion of the fluid dispenser just above the fragrance element and the portion of the mounting base just below the fragrance element substantially block the person from contacting the fragrance element.

13. The assembly of claim 12 wherein the outer diameter of the fragrance element is between about 70% and 95% of the corresponding outer diameter of the fluid dispenser and the corresponding diameter of the mounting base.

14. The assembly of claim 1 wherein the engagement feature on the portion of the fluid dispenser is a thread adapted to engage a threaded hole in the mounting base.

15. The assembly of claim 1 wherein the fluid dispenser comprises a container and a cap, and wherein the fragrance element is arranged in the assembly to release the fragrance into the air around the assembly when the cap is completely engaged to the container, thereby sealing a fluid inside the fluid dispenser.

16. The assembly of claim 1,
wherein the portion of the fluid dispenser with the engagement feature has a substantially convex bottom surface, which prevents the fluid dispenser from supporting itself in an upright position unless the engagement feature is engaged to the mounting base.

17. The assembly of claim 1 wherein the fluid dispenser comprises a manually actuated pump and spout assembly coupled to a cap, wherein measured amounts of fluid can be dispensed by manually pushing downwardly and releasing the manually actuated pump and spout assembly.

18. An assembly comprising:
a mounting base having an annular surface;
a fluid dispenser, which comprises: a container, a cap, an annular lip and a threaded protrusion adapted to engage the mounting base; and
a substantially annular fragrance element with surfaces that define an opening through which the threaded protrusion can extend,
wherein the fragrance element is positioned around the threaded protrusion and between the annular lip of the fluid dispenser and the annular surface of the mounting base, and
wherein the assembly is arranged such that, when the threaded protrusion is fully engaged to the mounting base, an outer surface of the fragrance element is exposed to release fragrance outside the assembly.

19. The assembly of claim 18 wherein the fragrance element comprises an absorbent material permeated with a fragrance.

20. The assembly of claim 19 wherein the absorbent material is a porous polyethylene.

21. The assembly of claim 19 wherein the absorbent material is paper.

22. The assembly of claim 19 wherein the absorbent material is further permeated with a malodor counteracting ingredient.

23. The assembly of claim 18 wherein the fragrance element has an outer diameter that is smaller than a corresponding outer diameter of a portion of the fluid dispenser just above the fragrance element and smaller than a corresponding outer diameter of a portion of the mounting base just below the fragrance element,
such that when a person grips the assembly near the fragrance element, the portion of the fluid dispenser just above the fragrance element and the portion of the mounting base just below the fragrance element substantially prevent the person from contacting the fragrance element.

24. The assembly of claim 18 wherein the fluid dispenser comprises a manually actuated pump and spout assembly coupled to the cap, wherein measured amounts of fluid can be dispensed by manually pushing downwardly and releasing the manually actuated pump and spout assembly.

25. An assembly comprising:
a fluid dispenser comprising a container and an annular lip;
a threaded protrusion formed on the container;
a mounting base for the fluid dispenser, the mounting base comprising: an annular surface and a threaded opening adapted to engage the threaded protrusion formed on the container;
a fragrance element with one or more surfaces that define an opening,
wherein the threaded protrusion extends through the opening in the fragrance element and engages the threaded opening in the mounting base, and wherein the assembly is arranged such that when the fragrance element is positioned between the annular lip of the fluid dispenser and the annular surface of the mounting base and the engagement feature on the fluid dispenser is fully engaged with the mounting base, an outer surface of the fragrance element is exposed to release fragrance outside the assembly.

26. The assembly of claim 25 wherein the fragrance element is substantially annular and comprises an absorbent material permeated with fragrance.

27. The assembly of claim 26 wherein the absorbent material is a porous polyethylene.

* * * * *